United States Patent [19]

Nuwayser

[11] Patent Number: 4,707,362
[45] Date of Patent: Nov. 17, 1987

[54] SUSTAINED RELEASE COMPOSITION

[75] Inventor: Elie S. Nuwayser, Wellesley, Mass.

[73] Assignee: Biotek, Inc., Woburn, Mass.

[21] Appl. No.: 702,008

[22] Filed: Feb. 15, 1985

[51] Int. Cl.⁴ ............................................. A61F 13/00
[52] U.S. Cl. .................... 424/433; 514/843; 514/964; 514/965; 514/967
[58] Field of Search ................ 424/19, 433; 514/843, 514/967, 964, 965

[56] References Cited

U.S. PATENT DOCUMENTS

| | | | |
|---|---|---|---|
| 3,639,561 | 2/1972 | Gordon et al. | 424/28 |
| 3,876,757 | 4/1975 | Scherm | 424/44 |
| 3,887,699 | 6/1975 | Yolles | 424/19 |
| 4,031,202 | 6/1977 | Laughlin et al. | 424/28 |
| 4,067,961 | 1/1978 | Laughlin | 424/15 |
| 4,145,408 | 3/1979 | Laughlin | 424/16 |
| 4,187,286 | 2/1980 | Marcus | 424/44 |
| 4,235,988 | 11/1980 | Fildes et al. | |
| 4,304,226 | 12/1981 | Drobish et al. | 128/127 |
| 4,317,447 | 3/1982 | Williams | |
| 4,322,399 | 3/1982 | Ahmad et al. | 424/44 |
| 4,384,003 | 5/1983 | Kazmiroski et al. | 514/967 X |
| 4,393,871 | 7/1983 | Vorhauer et al. | 609/58 |
| 4,402,693 | 9/1983 | Roseman et al. | 604/890 |
| 4,551,148 | 11/1985 | Riley et al. | 604/890 |

OTHER PUBLICATIONS

Barrier Methods, *Population Reports*, Series H, No. 5, (1979).
A. S. Lichtman, et al., *Contraception*, vol. 8, No. 4, Oct. 1973.

*Primary Examiner*—Leonard Schenkman
*Attorney, Agent, or Firm*—Hamilton, Brook, Smith & Reynolds

[57] ABSTRACT

A vehicle which provides rapid release of a drug and prolonged release of a drug is disclosed.

15 Claims, 2 Drawing Figures

SUSTAINED RELEASE COMPOSITION

TECHNICAL FIELD

This invention is in the fields of chemistry and biochemistry and in particular relates to drug delivery and to vaginal contraceptives.

BACKGROUND ART

Numerous methods of contraception are available today, including oral contraceptives, intra-uterine devices (IUDs), sterilization and vaginal spermicides. When taken according to directions, oral contraceptives provide protection which is nearly 100 percent effective. IUDs are almost equally effective and particularly appropriate for parous women. Sterilization is effective and has few apparent adverse effects for couples who want essentially permanent protection. Vaginal spermicides have been shown to be generally effective. If they are used correctly, spermicides can be more than 95 percent effective; even if not used correctly all the time, spermicides are apparently about 85 percent effective. A 1976 study of U.S. women using contraception showed that about 15 percent of spermicide users became pregnant within the first 12 months of spermicide use. In contrast, 2 percent of pill users and about 4 percent of IUD users became pregnant within the first 12 months of use. Barrier Methods, *Population Reports*, Series H, No. 5, H77-78. (1979).

Each of the available methods of contraception has disadvantages which must be considered in assessing their appropriateness for and acceptability to users. For oral contraceptives, important disadvantages are the need to take the pill on an ongoing basis and the numerous reports of adverse reactions associated with their use. IUDs have several problems associated with their use, including incorrect placement, dislodging after insertion, bleeding and pain. Sterilization requires a surgical procedure and one of its biggest advantages—its permanence—may prove to be a major disadvantage if decisions about childbearing are reversed. The major disadvantages of spermicidal contraceptives are that they must be used close to the time of intercourse; require a relatively long waiting period before they are effective; provide protection of relatively short duration; generally require re-application before each act of intercourse; and may leave a messy residue. These disadvantages, in addition to improper placement of the contraceptive in the vagina, are important causes of the failure of spermicides to provide protection as effective as that available from other methods.

Despite these disadvantages, vaginal spermicides do have distinct contraceptive advantages. For example, they are readily available as nonprescription formulations; can be used on an "as needed" basis; and produce few adverse physiological effects. As a result, they have considerable promise as an alternative to other available contraceptive methods.

There are at least seven different forms of vaginal spermicidal products available today: creams, jellies, foams, effervescent tablets, biodegradable soluble films, sponges and suppositories. Vaginal spermicide formulations consist of the spermicide dissolved in or mixed with an inert base. The inert base serves to carry the spermicide and hold it in the vagina; it may also act as a barrier which interferes with direct contact between the sperm and cervical mucous. The spermicide is a chemically active ingredient which incapacitates the sperm.

There have been countless attempts to provide effective protection through the use of vaginal spermicides, as evidenced by the extensive literature and the number of patented formulations and commercially available products. For example, two types of foam are available: foams supplied in pressurized cans and foaming tablets or suppositories. Both types have the disadvantages enumerated: application is necessary prior to intercourse; only short-term protection is provided; re-application is necessary, etc. Foaming tablets require large amounts of moisture in the vagina and may take as long as 20 minutes to ensure foaming action. Some suppositories also require large quantities of vaginal fluid and, because they have melting points higher than the vaginal temperature, do not consistently release all of the active ingredient.

There have been attempts to solve some of the problems associated with vaginal spermicides. Kazmiroski et al (U.S. Pat. No. 4,384,003) disclose a vaginal contraceptive suppository which is said to have both rapid release of an active ingredient and prolonged effectiveness. The suppository disclosed is comprised of a mixture of sodium starch glycolate, a thickening agent, and a vegetable oil base combined with a spermicide. The resulting composition is said to release the active ingredient in less than 15 minutes and maintain effectiveness for up to 6 hours. The extended duration of spermicidal action which is apparently due to the production of a thick, non-runny paste which will not leak from the vaginal orifice.

Laughlin et al. (U.S. Pat. No. 4,031,202) disclose a controlled release article which is claimed to provide substantially immediate release of a material releasably affixed on the outside of the article and subsequent release of compounds contained within the article. The immediate release agent can be a spermicide and is affixed on the outer surface of a container which releasably encloses a solution of a micelle-forming compound. The compound is said to be able to migrate through a microporous membrane and provide an effective spermicide concentration over a 21-day period. The article is said to provide contraceptive protection when allowed to remain in the vagina between menstrual periods.

Contraceptive films, which are water soluble films, have been developed for use as vaginal spermicides. The effectiveness of these C-films, as they are called, is unclear. Studies with a flat sheet of this dissolving film showed pregnancy rates of 9 to 62 per 100 woman-years. Barrier Methods, *Population Reports*, Series H, No. 5, H103 (1979). Such contraceptive film is being modified for easy, effective use by the male partner. Fast-dissolving films used in making these water-soluble or spermicidal condoms are said to release the active agent quickly and thus provide rapid spermicidal action. There is, however, no long-term protection and a new film must be used each time intercourse occurs.

Long-term spermicide release can be achieved through the use of nondissolving delivery systems, such as vaginal rings or cervical caps which release spermicides. Neither of these configurations provides for immediate or at least quick release of spermicide.

Drobish et al. (U.S. Pat. No. 4,304,226) disclose a cervical cap to be used to deliver spermicide in the vagina. The cap is claimed to be designed to remain in the vagina between menstrual periods, during which time it is to provide release of the spermicide.

Although much effort has been expended toward developing a vaginal spermicide which is acceptable to the user and effective in providing contraceptive protection, there is at present no vaginal spermicide which does not suffer from one or more of the aforementioned disadvantages. Currently available formulations which are used on an "as needed" basis require a relatively long time after insertion before they provide effective spermicide concentrations, provide only short-term protection and leave a messy residue. Spermicides which are delivered continuously over a period of several days or weeks (e.g., from a vaginal ring or cervical cap) provide no immediate protection and are released during times when no protection is necessary, thus unnecessarily exposing the user to the long-term side effects of spermicides.

What is needed, therefore, is a means of providing an immediate release of effective concentrations of spermicide upon placement in the vagina and a prolonged release of the spermicide. This dual approach is necessary to provide protection against the first ejaculate, thus eliminating the need for a waiting period between insertion and intercourse, and further protection for an extended period, thus eliminating the need for reapplication before each act of intercourse (as well as for insertion immediately prior to intercourse). Although there are formulations presently available for use on an "as needed" basis, none provides this highly desirable combination of quick release of effective spermicide concentrations followed by prolonged spermicide release which provides contraceptive protection.

DISCLOSURE OF THE INVENTION

The subject of this invention is a vehicle for drug delivery which provides rapid release and sustained release of a drug or drugs and a method for making such a vehicle.

In one embodiment, the vehicle comprises a suppository body made of a material which melts at the temperature of the body cavity into which the suppository is inserted and having a drug or drugs dispersed in it and at least one film insert which contains a drug or drugs and is made of a material which slowly erodes at the temperature of the body cavity, thus releasing the drug or drugs over a prolonged period of time.

In another embodiment, the vehicle provides rapid release and prolonged release of spermicide at effective concentrations. In this embodiment, the vehicle comprises a suppository body made of polymers which melt at the temperature of the vagina and having a spermicide, such as nonoxynol-9 dispersed throughout and at least one film insert which has a spermicide dispersed throughout and is made of water-soluble polymers which are slowly eroded, thus releasing the spermicide. The spermicide in the film insert can be the same as that in the suppository body or different. In a particular embodiment, the suppository body is made of polyethylene glycol and the film insert is made of polyvinyl alcohol and glycerin; the spermicide dispersed in the two components is nonoxynol-9.

This invention is also a method for making the vehicle for drug delivery. According to this method, a suppository base is made of a hydrophilic polymer and a drug or drugs; a film is made of water-soluble polymers, drug or drugs and a film plasticizer; and the film is incorporated into the suppository base. The vaginal contraceptive of this invention has many highly desirable attributes. For example, it is portable and convenient to use both immediately before intercourse or ahead of time; effective at the temperature of the vagina; delivered quickly and directly to the cervical opening; bioerodible; and non-toxic. In addition, its prolonged action not only permits early placement, but also affords protection against more than one act of intercourse.

Thus, the vaginal contraceptive of this invention has the highly desirable ability to provide contraceptive protection immediately after insertion, as well as to provide effective protection for a prolonged period of time.

BEST MODE OF CARRYING OUT THE INVENTION

Figure 1:
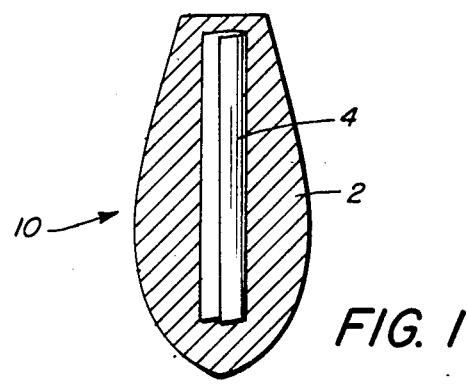
FIG. 1 is a cross-sectional view of a composite suppository and shows the suppository body with a single film positioned along the longitudinal axis thereof.
Figure 2:
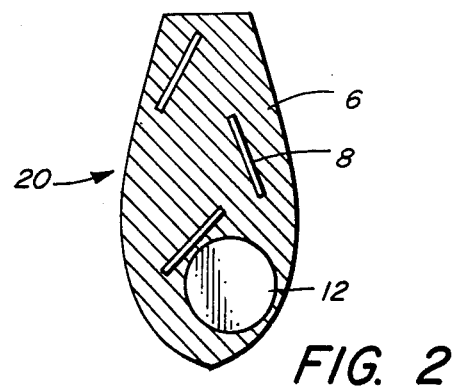
FIG. 2 is a cross-sectional view of another embodiment of a composite suppository and shows a suppository body with a plurality of pieces of film distributed throughout.

The subject of this invention is a vehicle for providing both rapid release and prolonged release of a drug and a method of making the vehicle. The two major elements of the vaginal contraceptive which is the subject of this invention are a suppository body, which melts at body temperature, and the bioerodible film insert. Each also includes a spermicide. Two embodiments of this invention are shown in the figures. FIG. 1 shows vaginal contraceptive 10, which has a suppository body 2 and a film insert 4. FIG. 2 shows vaginal contraceptive 20, which has a suppository body 6 and a number of film inserts 8 and 12.

The vehicle may, in the alternative, be used for the delivery of a drug other than a spermicide. In that case the suppository body and the film insert are made in the same way as will now be described for the vaginal spermicide but a drug other than a spermicide is incorporated into each. The drug contained in the suppository body can be the same as that contained in the film insert or different. The invention will now be described with reference to the FIGURES.

The size of the suppository body of this invention varies according to the intended use. Typically, it is from about 10mm to about 35 mm in length when its intended use is as a vaginal contraceptive. Its weight can range from about 1.5 grams to about 4.5 grams. In one embodiment of this invention, the suppository body is about 14 mm in diameter and about 30 mm in length and weighs approximately 3.9 grams.

The film insert size is varied according to its use and the number of inserts to be incorporated into the suppository body. Typically, the film has a thickness of about 1 mil to about 40 mils when it is a component of a vaginal contraceptive. The total surface area (both sides) of the film insert can be varied according to need and typically is from about 50 mm$^2$ to about 2000 mm$^2$ FIG. 1 shows one embodiment in which a single film insert 4 is incorporated into suppository body 2; the film insert is 20 mm x 20 mm, has a thickness of 1 mil and has a total surface area (both sides of the film) of 800 mm$^2$. FIG. 2 shows another embodiment in which a number of film inserts 8 and 12 is incorporated into suppository body 6; each insert is about 6.25 mm in diameter, has a thickness of 18 mil and has a surface area of 61.4 mm$^2$ (both sides). The number of inserts of smaller size incorporated into the suppository body can be varied and in one embodiment, the total surface area (both sides) of the film inserts is about 2000 mm$^2$.

The shape of the suppository body can generally be described as bulbous, conical or cylindrical and is designed for ease of insertion. FIGS. 1 and 2 illustrate one shape which can be used for the suppository of this invention. It is generally a bulbous configuration with one end cylindrical in shape.

The film insert material can be any shape (e.g., square, rectangular, circular, triangular) appropriate for incorporation into the suppository body. The film insert may consist of a single piece of film or a number of small pieces. In the embodiment illustrated in FIG. 1, a single piece of film is positioned in the suppository body along its longitudinal axis and can be loosely folded like an open cylinder. In the embodiment illustrated in FIG. 2, numerous pieces of film are distributed throughout the suppository body.

The suppository body is made from hydrophilic materials which melt at or below the temperature of the body cavity into which it is inserted. For example, the materials used in making the suppository body will melt at temperatures at or below vaginal temperature, which is generally 36°–37° C. Typically, the materials used are water-soluble. There is a wide variety of such materials which can be used. Particularly appropriate in formulating the material to be used in forming the suppository body are polyethylene glycols, which are long-chain polymers of ethylene oxide. The general formula for such polymers is $HOCH_2(CH_2OCH_2)_xCH_2OH$; polymers with molecular weights above 1000 are wax-like solids at room temperature. By combining two or more polyethylene glycols with different water solubilities and melting points, it is possible to make suppository bodies with different characteristics (e.g., heat stability, water solubility and dissolution rates). There are several polyethylene glycol polymers, sold as Carbowax and Polyglycols, which are approved for use in making suppositories.

In one embodiment of this invention, polyethylene glycol 1450 and polyethylene glycol 1000 are used in a 1:1 ratio to make a suppository body which melts at or below the temperature of the vagina.

There are also nonionic surface active agents, which are chemically similar to the polyethylene glycols, which can also be used in making suppositories. For example, surface active agents (surfactants), such as polyoxyethylene sorbitan fatty acid esters (e.g., Tween), polyoxyethylene stearates (e.g., Myrj) and sorbitan fatty acid esters (e.g., Span, Arlacel) can be used (alone, together or in combination with other materials) to make suppository bodies which have different melting points.

The suppository body of this invention melts and thus releases the spermicide incorporated into it, and the melting can be accelerated by the incorporation of a foaming agent into the suppository body. This foaming agent can be any chemical or combination of chemicals which can produce a gas. In aqueous surroundings, the combination of alkali metal carbonates or bicarbonates with di- or polycarboxylic acid results in a chemical reaction, one product of which is a gas (i.e., carbon dioxide). For example, sodium bicarbonate and citric acid anhydrous (sodium citrate) can be used to produce carbon dioxide. Upon contact with water, this reaction is used to produce the foaming action and effervescence which hasten the release of the spermicide from the suppository and accelerate its disintegration.

The film insert which serves to release the spermicide over an extended period of time is comprised of water soluble polymers and is bioerodible. The term bioerodible refers to the twofold process by which the film slowly loses its integrity: it is physically worn away gradually or by degrees and also undergoes dissolution. The properties of the materials used in making the film insert of the vaginal spermicide have been modified to result in the release of the spermicide at an effective concentration over a prolonged period (i.e., up to 24 hours).

The bioerodible material may be one of at least three major types: natural products, modified natural products and synthetic products. Natural products, derived from animal and vegetable sources, include starches, dextrins, alginates, natural gums, gelatin, casein and agar. Modified natural products, as the term suggests, are natural products whose chemical structure has been altered. These include the alkyl and hydroxyalkyl ethers of cellulose and starch, ionic starches, carboxylates, carboxymethyl cellulose and the mixed ethers of starch and cellulose. The synthetic water soluble polymers include materials such as polyvinyl alcohols and polyvinyl pyrrolidone in the original form or after physical or chemical modification of the polymers.

In one embodiment, the bioerodible material is polyvinyl alcohol whose properties have been modified so that the spermicide (e.g., nonoxynol-9 octoxynol, menfegol) in the film is slowly released (i.e., at a rate of 10–20 mgm over a 16-hour period) This can be as high as 200 mgm of spermicide over a period of up to 24 hours. An example of such a polyvinyl alcohol is Vinol, supplied by Air Products and Chemicals, Inc. There are several methods available for adjusting or modifying the properties and solubility of polyvinyl alcohol films, including heat treatment, exposure to light, chemical treatment and addition of plasticizers and other additives, such as foam stabilizers and film formers. In addition, properties can be adjusted or modified by reactions with chemicals such as aldehydes, ketones and inorganic compounds.

In the vaginal contraceptive of the present invention, both the suppository body and the film insert comprise, in addition to the components listed above for each, a spermicide. There are several spermicides which can be used, including surfactants, such as nonoxynol-9 (nonylphenoxypoly(ethyleneoxy)ethanol); octoxynol-9 and menfegol. Examples of other spermicides which can be used are: dodecaethylene glycol monolaurate; laureth 10S; methoxypolyoxyethyleneglycol 550 laurate; phenylmercuric acetate and phenylmercuric nitrate.

The spermicide is incorporated into the suppository body and the film insert, for example by being dissolved or dispersed, while each is being made. Release of the spermicide from the suppository body, as mentioned, occurs as it dissolves in the vagina. After the suppository body has dissolved, the film is released. Release of the spermicide from the film occurs by a combined process of diffusion and bioerosion. The film insert, once released from the suppository body, adheres to the mucosal surfaces of the vagina and is not easily palpable during intercourse.

In one embodiment, the active ingredient is nonoxynol-9, which is present in spermicidally effective concentrations. For example, about 300 mgm of nonoxynol-9 is present in one embodiment of the composite vaginal spermicide (suppository body and film insert). In this embodiment, the non-oxynol-9 content of the base can be as high as about 10% by weight and the nonoxynol-9 content of the film can be as high as about 30% by weight.

The vaginal contraceptive, in one embodiment of this invention, releases approximately 20% of the spermicide in the contraceptive agent within about 1 minute after insertion. This rapid release occurs because the suppository body is made from the water-soluble materials (previously described) which dissolve at the temperature of the vagina and because the release is accelerated by the foaming agent. In one embodiment, the bioderodible film released as a result of the dissolving of the suppository body provides release of at least 0.2 mgm of nonoxynol-9 per hour over a period up to 24 hours. This is the minimum rate recommended by the WHO Task Force on Vaginal and Cervical Devices for Fertility Regulation. G. Benagiano, Proceedings of the Drug Delivery System Workshop. H. Gabelnick (ed.), DHEW Publication No. (NIH) 77-1238, p. 402.

In addition to water-soluble polymers, foaming agent and spermicide, the suppository body of this invention may also be comprised of a cooling additive, a fragrance and an antibacterial agent or preservative.

The film insert may have, in addition to the water-soluble polymers and spermidicide, a film plasticizer (e.g., glycerin or propylene glycol). The film plasticizer serves the purpose of making the film more flexible.

The suppository of this invention could, of course, be used to deliver substances other than spermicides and can thus be used for purposes other than contraception. Possible additional uses include treatment of genital or vaginal infections (e.g., monoliasis); administration of steroid hormones (e.g., estradiol for therapy in patients with osteoporosis or progesterone for amelioration of premenstrual syndrome); delivery of antiasthmatics (e.g., bronchiodilating agents) and administration of local anesthetics.

The following examples are presented to illustrate the invention and for that purpose only. They are not intended to be limiting in any way.

EXAMPLE 1

Foaming Suppository

An anhydrous foaming suppository which has water soluble polyethylene glycol 1000 and polyethylene glycol 1450 as the base materials and nonoxynol-9 as the spermicide is made and has the following composition:

|  | Percent by Weight | Grams needed to Make 10 Suppositories |
| --- | --- | --- |
| Polyethylene glycol 1000 NF | 56.1 | 18.50 |
| Polyethylene glycol 1450 NF | 18.7 | 6.20 |
| Nonoxynol-9 | 5.0 | 1.65 |
| Citric Acid Anhydrous U.S.P. | 10.0 | 3.30 |
| Sodium bicarbonate U.S.P. | 9.2 | 3.05 |
| Sodium citrate U.S.P. | 1.0 | 0.33 |

The suppository is made according to the following method: A base mixture is made by melting weighted quantities (see above) of polyethylene glycol 1000 and polyethylene glycol 1450 in a water bath or suitable reaction vessel surrounded by a heating mantle. Citric acid anhydrous and sodium citrate are added to the cooling base (at a temperature of about 45° C.) of the polyethylene glycol. The combination is allowed to cool until it is just above the congealing point (about 43° C.). Weighted quantitites (see above) of nonoxynol-9 and sodium bicarbonate are mixed together with a spatula to form a homogeneous paste. A fragrance can also be mixed in with this paste at the same time. The paste is then added to the molten base and mixed with a motorized stirrer slightly above the congealing temperature (about 43° C.). The combination is mixed to make a uniform and homogeneous mixture. When the entire mixture begins to congeal (about 41° C.), it is poured into chilled metal or plastic molds and refrigerated (4° C.) for about 20 minutes. The excess mixture is removed from the suppositories and they are again refrigerated (4° C.) for 24 hours. After 24 hours, the suppositories are removed from the molds, and stored under refrigeration until needed.

The physical properties of suppositories made according to this method were determined. The measurements included weight, spermicide release rate, and melting point. The characteristics of the prototype suppository are as follows:

weight: 1.65 grams
melting point: 35°-38° C.

EXAMPLE 2

Bioerodible Films

Films were made from either a fully hydrolysed high molecular weight hot water-soluble polyvinyl alcohol (e.g., Vinol 350) or from a partially hydrolysed medium molecular weight polyvinyl alcohol (e.g., Vinol 523). The nonoxynol-9 was mixed with the polymer solutions to a concentration of 20% and the films were placed in trays at room termperature and dried for 1 to 10 days.

Samples of these films were placed in 50 ml of distilled water and aliquots were taken over time. Release of nonoxynol-9, as represented by its presence in the aliquots, was determined by UV spectrophotometry. Results showed that the partially hydrolysed film released all of the spermicide in two hours and the fully hydrolysed film released 50% of the spermicide in 20 hours.

A mixture of 75% fully hydrolysed polyvinyl alcohol with 25% of the partially hydrolysed polyvinyl alcohol released 78% of the drug during the first two hours.

In all tests, the films were evaluated in 50 ml of water, the fluid volume in the vagina is much less than this (e.g., about 5–10 ml).

Heat treatment of a partially hydrolysed film (60 min. @180° C.) modified its crystalline composition. It also produced a dramatic decrease in the rate of spermicide release. In this heat treated partially hydrolysed film 40% of the drug was released after 2 hours, compared with 96% release from the untreated film.

EXAMPLE 3

Composite Suppository

A composite contraceptive suppository with a bioerodible film within was made according to the following formulation:

COMPOSITION OF CONTRACEPTIVE SUPPOSITORY BASE

| | Percent by Weight | Grams Needed to Produce 500 Suppositories |
|---|---|---|
| Polyethylene Glycol 1450 N.F. | 37.15 | 743.0 |
| Polyethylene Glycol 1000 N.F. | 37.15 | 743.0 |
| Nonoxynol-9 | 5.5 | 110.0 |
| Sodium Citrate U.S.P. | 1.0 | 20.0 |
| Tartaric Acid N.F. | 10.0 | 200.0 |
| Sodium Bicarbonate U.S.P. | 9.2 | 184.0 |
| | 100.0 | |

COMPOSITION OF FILM CONTAINING NONOXYNOL-9

| Ingredients | Percent by Weight |
|---|---|
| Polyvinyl Alcohol U.S.P. | 67 |
| Glycerin U.S.P. (20% w/w Glycerin in PVA) | 13 |
| Nonoxynol-9 (30% w/w Nonoxynol-9 in PVA) | 20 |
| | 100 |

INDIVIDUAL SUPPOSITORY COMPOSITION

| | Percent by Weight | Calculated grams |
|---|---|---|
| Polyethylene Glycol 1450 N.F. | 33.6 | 1.3186 |
| Polyethylene Glycol 1000 N.F. | 33.6 | 1.3186 |
| Nonoxynol-9* | 7.4 | 0.2890 |
| Sodium Citrate U.S.P. | 0.9 | 0.0355 |
| Tartaric Acid N.F. | 9.1 | 0.3549 |
| Sodium Bicarbonate U.S.P. | 8.3 | 0.3265 |
| Polyvinyl Alcohol U.S.P. (film) | 5.7 | 0.2216 |
| Glycerin U.S.P. (film plasticizer) | 1.4 | 0.0554 |
| | 100.0 | 3.9201 |

*total quantity in suppository and film

This composite formulation is made according to the following method: Weighed quantities (as designated above for base) of polyethylene glycol 1000 and polyethylene glycol 1450 are melted together as in Example 1. Citric acid anhydrous and sodium citrate are added to the cooling mass (at a temperature of about 45° C.) of polyethylene glycol. The combination is allowed to cool until it is slightly above the congealing point (about 43° C.). Weighed quantities (see above) of nonoxynol-9, and sodium bicarbonate are mixed together to form a homogeneous paste. The above paste is incorporated into the molten base at a temperature slightly above the congealing temperature (about 43° C.) and mixed to disperse uniformly and homogeneously. When the entire mixture begins to congeal (about 41° C.), plastic molds are filled to about one half their total volume. The bioerodible film of Example 2 is added with forceps and the molds are then filled with additional base mixture and refrigerated (4° C.) for at least one hour. The excess suppository base is then removed and the ends of the molds heat sealed. After sealing, the suppositories are refrigerated until needed.

INDUSTRIAL APPLICABILITY

The composition of this invention can be used for the delivery of drugs and active ingredients. For example, it can be used for the treatment of a variety of diseases, for the delivery of spermicidally active ingredients to provide contraceptive protection and for the local administration of anesthetics.

EQUIVALENTS

Those skilled in the art will recognize, or be able to ascertain using no more than routine experimentation, many equivalents to the specific embodiments of the invention described herein. Such equivalents are intended to be encompassed by the following claims.

I claim:

1. A vaginal contraceptive having both rapid release and prolonged release of spermicide at effective concentrations, comprising:
   a. a suppository body, comprising hydrophilic material which melts at or below the temperature of the vagina and having incorporated therein a spermicide, the spermicide being released therefrom at effective contraceptive concentrations within the first minute after placement of the contraceptive in the vagina; and
   b. at least one film insert in the suppository body, the film insert comprising a water-soluble polymer which is bioerodible and having incorporated therein a spermicide which is released at effective contraceptive concentrations over a period of up to 24 hours after placement of the contraceptive in the vagina.

2. The vaginal contraceptive of claim 1 wherein the suppository body is comprised of hydrophilic material selected from the group consisting of polyethylene glycols, polyoxyethylene sorbitan fatty acid esters, polyoxyethylene stearates and sorbitan fatty acid esters and the film insert is comprised of a water-soluble polymer selected from the group consisting of starches, dextrins, alginates, nature gums, gelatin, casein, agar, alkyl ethers of cellulose, hydroxyalkyl ethers of cellulose, alkyl ethers of starch, hydroxyalkyl ethers of starch, ionic starches, carboxylates, carboxymethyl cellulose, mixed ethers of starch, mixed ethers of cellulose, polyvinyl alcohols and polyvinyl pyrrolidone.

3. A vaginal contraceptive which releases effective contraceptive concentrations of a spermicide incorporated therein within the first minute after placement of the contraceptive in the vagina and for a period of up to 24 hours after placement of the contraceptive in the vagina, comprising:
   a. a suppository body comprising a hydrophilic material which melts at or below the temperature of the vagina, a foaming agent and spermicide; and
   b. at least one film insert within the suppository body, comprising polyvinyl alcohol or polyvinyl pyrrolidone, spermicide and a plasticizer, which releases the spermicide over a period of up to 24 hours after placement of the contraceptive in the vagina.

4. The vaginal contraceptive of claim 3, wherein polyethylene glycol is the hydrophilic material; the foaming agent comprises (a) at least one alkali metal carbonate or at lease one alkali metal bicarbonate and (b) at lease one dicarboxylic acid, or salt thereof, or at least one polycarboxylic acid, or salt thereof, and the plasticizer is glycerin or propylene glycol, the vaginal contraceptive comprosing from about 60% to about 85% polyethylene glycol by weight; from about 5% to about 15% by weight of at least one alkali metal carbonate or at least one alkali metal bicarbonate; from about 5% to about 15% by weight of at least one dicarboxylic acid, or salt thereof, or at least one polycarboxylic acid, or salt thereof; up to about 10% by weight of a spermicide; from about 4% to about 8% by weight of polyvinyl alcohol or polyvinyl pyrrolidone; and about 1.4% by weight of glycerin or propylene glycol.

5. The vaginal contraceptive of claim 4, which is comprised of polyethylene glycol 1450 and polyethylene glycol 1000 in a 1:1 ratio; the spermicide is nonoxynol-9; about 1% by weight of sodium citrate; about 9% by weight of tartaric acid; about 8% by weight of sodium bicarbonate; from about 5% to about 7% by weight of polyvinyl alcohol and from about 1% to about 2% by weight of glycerin.

6. A vaginal contraceptive having both rapid release and prolonged release of spermicide at effective contraceptive concentrations and having a suppository body which melts at or below the temperature of the vagina and at least one film within the suppository body which provides prolonged release of spermicide at effective concentrations, comprising about 67.2% by weight of polyethylene glycol; about 7.4% by weight of a spermicide; about 18.3% by weight of a foaming agent; about 5.7% by weight of polyvinyl alcohol and about 1.4% by weight of a film plasticizer.

7. The vaginal contraceptive of claim 6 in which polyethylene glycol 1450 and polyethylene glycol 1000 are present in equal amounts; the spermicide is nonoxynol-9; and the foaming agent is comprised of sodium citrate, tartaric acid and sodium bicarbonate, the sodium citrate being present as approximately 0.9% of the total contraceptive weight, the tartaric acid being present as approximately 9.1% of the total contraceptive weight and the sodium bicarbonate being present as approximately 8.3% of the total contraceptive weight.

8. A vehicle for drug delivery which provides rapid release and sustained release of a drug, the vehicle comprised of:
   a. a suppository body comprising hydrophilic material which melts at or below body temperature, the suppository body releasing a drug incorporated therin within the first minute after contact of the suppository body with an aqueous medium at body temperature; and
   b. at least one film insert in the suppository body, the insert releasing a drug incorporated therein over a period of up to 24 hours after contact with an aqueous medium at body temperature.

9. A vehicle for drug delivery which provides rapid release and sustained release of a drug and which is inserted into a body cavity, the vehicle comprising:
   a. a suppository body comprising a material which melts at the temperature of the body cavity and dispersed therethrough a drug, the material which melts at the temperature of the body cavity being selected from the group consisting of: polyethylene glycols, polyoxyethylene sorbitan fatty acid esters, polyoxyethylene stearates, and sorbitan fatty acid esters; and
   b. at least one film insert comprising a material which slowly erodes at the temperature of the body cavity and a drug, the material which slowly erodes being selected from the group consisting of: starches, dextrins, alginates, natural gums, gelatin, casein, agar, alkyl ethers of cellulose, hydroxyalkyl ethers of cellulose, alkyl ethers of starch, hydroxyalkyl ethers of starch, ionic starches, carboxylates, carboxymethyl cellulose, mixed ethers of starch, mixed ethers of cellulose, polyvinyl alcohols and polyvinyl pyrrolidone, whereby, upon insertion into a body cavity, the suppository body provides rapid release of said drug and the film insert provides sustained release of said drug.

10. A method of making a vaginal contraceptive which is comprised of a suppository body which melts at or below the temperature of the vagina and at least one film within the suppository body having both rapid release and prolonged release of spermicide at effective contraceptive concentrations, comprising the steps of:
   a. molding a suppository body comprised of a spermicide and polyethylene glycol;
   b. making a film comprised of a spermicide and polyvinyl alcohol; and
   c. incorporating a film formed in (b) into the body formed in (a).

11. A method of making a vaginal contraceptive which is comprised of a suppository body which melts at or below the temperature of the vagina and at least one film within the suppository body, having both rapid release and prolonged release of spermicide at effective contraceptive concentrations, comprising the steps of:
   a. molding a suppository body comprising a hydrophilic polymer, a spermicide and a foaming agent;
   b. making a film comprised of a water-soluble polymer, a spermicide and a film plasticizer; and
   c. incorporating the film formed in (b) into the suppository body of (a).

12. A method of making a vaginal contraceptive which is comprised of a suppository body which melts at or below the temperature of the vagina and at least one film within the suppository body, having both rapid release and prolonged release of spermicide at effective contraceptive concentrations, comprising the steps of:
   a. combining polyethylene glycol, nonoxynol-9 and a foaming agent to form a homogeneous mixture;
   b. forming a suppository body by molding the homogeneous mixture;
   c. combining polyvinyl alcohol nonoxynol-9 and a film plasticizer;
   d. forming a film of the combination produced in (c); and
   e. incorporating the film formed in (d) into the suppository formed in (b).

13. The method of claim 12 in which the polyethylene glycol is selected from the group consisting of polyethylene glycol 1450 and polyethylene glycol 1000; the foaming agent is comprised of sodium citrate, tartaric acid and sodium bicarbonate; and the film plasticizer is glycerin.

14. A method of making a vaginal contraceptive having both rapid release and prolonged release of spermicide at effective contraceptive concentrations, comprising the steps of:
   a. forming a base mixture by melting polyethylene glycol 1450 and polyethylene glycol 1000 in a 1:1 ratio;
   b. cooling the base mixture;
   c. combining cooled base bixture, nonoxynol-9 and a foaming agent in sufficient quantities to produce a combination comprising from about 50% by weight to about 60% by weight inclusive of cooled base mixture, from about 5% by weight to about 6% by weight, inclusive of nonoxynol-9 and about 20% by weight of a foaming agent;
   d. molding the combination of (c) to form a suppository body;
   e. combining about 67 wt % polyvinyl alcohol; about 13 wt % glycerin and about 20 wt % nonoxynol-9;

f. forming a film of the combination produced in (d);
g. incorporating the film formed in (f) into the suppository body formed in (d); and
h. refrigerating the product formed in g. at a temperature of about 4° C. for about 1 hour.

15. The vaginal contraceptive of claim 2 wherein the spermicide is selected from the group consisting of nonylphenoxypoly(ethyleneoxy) ethanol, octoxynol-9, menfegol, dodecaethylene glycol monolaurate, phenylmercuric acetate and phenylmercuric nitrate.

* * * * *